United States Patent [19]
Choi et al.

[11] Patent Number: 6,143,885
[45] Date of Patent: *Nov. 7, 2000

[54] PREPARATION OF BETA-METHYL CARBAPENEM INTERMEDIATES

[75] Inventors: Woo-Baeg Choi, North Brunswick; Jaemoon Lee, Edison; Joseph E. Lynch, Plainfield; Paul J. Reider, Westfield; Ralph P. Volante, Cranbury, all of N.J.

[73] Assignee: Merck & Co., Inc., Rahway, N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/128,638

[22] Filed: Jul. 28, 1998

Related U.S. Application Data

[63] Continuation of application No. 09/128,638, Jul. 28, 1998
[60] Provisional application No. 60/058,002, Aug. 27, 1997.
[51] Int. Cl.$^7$ .............................. C07D 205/08; C07F 7/18
[52] U.S. Cl. ........................................................... 540/200
[58] Field of Search ............................................. 540/200

[56] References Cited

U.S. PATENT DOCUMENTS

| | | | |
|---|---|---|---|
| 4,933,333 | 6/1990 | Sunagawa et al. | 514/192 |
| 4,943,569 | 7/1990 | Sunagawa | 514/210 |
| 4,960,879 | 10/1990 | Uyeo | 540/200 |
| 4,962,103 | 10/1990 | Sunagawa et al. | 514/210 |
| 5,011,832 | 4/1991 | Dininno et al. | 514/210 |
| 5,034,384 | 7/1991 | Greenlee et al. | 514/210 |
| 5,122,604 | 6/1992 | Sunagawa et al. | 540/350 |

FOREIGN PATENT DOCUMENTS

| | | |
|---|---|---|
| 2183236 | 11/1986 | United Kingdom . |
| 2183236 | 6/1987 | United Kingdom . |

OTHER PUBLICATIONS

Hu, J. Org. Chem. 63, 1719–1723, 1988.
Shiozaki, Journal of Antibiotics 37, 57, Jan. 1984.
Uyeo, Tet Letters 35(25) 4377, 1994.
Uyeo, et al, "Practical Sterocontrolled Synthesis of 2–Functionalized–methyl–1B–methylcarbapenems", Tetrahedron Letters, vol. 35, No. 25, pp. 4377–4378, 1994.
Shiozaki, et al, "Synthesis and Biological Activities of New Carbapenem Derivatives", The Journal of Antibiotics, vol. XXXVII, No. 1, pp. 57–62, 1984.
Hu, et al, "Synthesis of 2–(Hydroxymethyl)– 1B–methylcarbapenem. Chemoselective Orgnometallic Addition to 3–Substituted 4–[(R)–1–Carboxyethyl]azetidin–2–one", J. Org. Chem., vol. 63, No. 5, 1998.
T. Shibata et al., *Tetrahedron Letters*, 26(39), pp. 4739–4742 (1985).
Y. Nagao, *J. Am. Chem. Soc.* 108, pp. 4673–4675 (1986).
T. Iimori and M. Shibassaki, *Tetrahedron Letters*, 27(19), pp. 2149–2152 (1986).
M. Endo, *Can J. Chem.*, 65, pp. 2140–2145 (1987).
M. Endo, and R. Broghini, *Can. J. Chem.*, 66 pp. 1400–1404 (1988).
F. Shirai and T. Nakai, *Chem. Ltrs* pp. 445–448 (1989).
A. V. Rama et al., *Tetrahedron Letters* 31(2) pp. 271–274, (1990).
D.R. Bender et al., *J. Org. Chem.*, 57, pp. 2411–2418 (1992).
M. Kitamura et al. *Tetrahedron Letters.*, 31(4) pp. 549–552, (1990).
M. Imuta et al. *Chem. Phar. Bull.*, 39(3), pp. 672–678 (1991).
M. Imuta et al. *Chem. Phar. Bull*,39(3), pp. 663–671 (1991).
L. G. Wade, Jr., *Org. Chem. 2d Ed.*, Pretice Hall pp. 1012–1019 (1991).

*Primary Examiner*—Mark L. Berch
*Attorney, Agent, or Firm*—James M. Hunter, Jr.; Mark R. Daniel

[57] ABSTRACT

The instant invention relates to a compound of the formula:

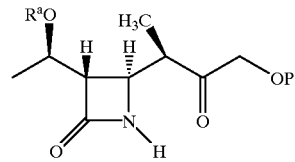

wherein $R_a$ and P are:
 (a) hydrogen,
 (b) methyl, or
 (c) a hydroxy protecting group
and an efficient process for its synthesis characterized by combining a ketoester with an acid and a catalyst at a temperature of from about 0° to about 50° C. and from about 0 to 500 psig to produce the above compound.

26 Claims, No Drawings

PREPARATION OF BETA-METHYL CARBAPENEM INTERMEDIATES

REFERENCE TO RELATED APPLICATION

This application claims the benefit of U.S. Provisional Application Serial No. 60/058,002, filed Aug. 27, 1997 which is continuation application claims the benefit of application Ser. No. 09/128,638, filed Jul. 28, 1998.

BACKGROUND OF THE INVENTION

The invention disclosed herein concerns a beta-methyl-hydroxymethyl ketone, and process for synthesis thereof, which is a key intermediate used in making beta-methyl carbapenems. 1-beta methyl carbapenem antibiotics, are particularly well known for treating a broad spectrum of gram-negative and gram-positive bacterial infections. See for example U.S. Pat. No. 4,962,103 issued Oct. 9, 1990; U.S. Pat. No. 4,933,333; U.S. Pat. No. 4,943,569; U.S. Pat. No. 5,122,604; U.S. Pat. No. 5,034,384 and U.S. Pat. No. 5,011,832.

Numerous routes to beta-methyl carbapenem intermediates of formula 6 have been cited in the literature:

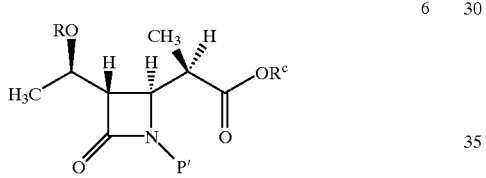

6

*Tetrahedron Letters*, Vol. 26, No. 39, pp 4739–4742, 1985; *J. Am. Chem. Soc.* 1986, 108, 4673–3675; *Tetrahedron Letters*, Vol. 27, No. 19, pp 2149–2152, 1986; *Can. J. Chem.* 65, 2140 (1987); *Can. J. Chem.* 66, 1400 (1988); *Chemistry Letters*, pp 445–448, 1989; *Tetrahedron Letters*, Vol. 31, No. 2, pp 271–274, 1990; *Tetrahedron Letters*, Vol 31, No. 4, pp 549–552, 1990; *J. Org. Chem.* 1992, 57, 2411–2418; and the like.

Previous methods of stereoselective preparation of beta-methyl carbapenems include:

(1) hydrogenation of a 4-(2-propenyl) substituted azetidinone.

(2) stereoselective protonation of an enolate ion (3) reaction of 4-acetoxyazetidinone with a chiral enolate.

These methods require difficult multi-step preparation, tedious manipulation of highly reactive intermediates at low temperature, or use of expensive reagents.

The instant invention discloses an efficient process for the synthesis of beta-methyl intermediates with high stereoselectivity from readily available starting materials.

SUMMARY OF THE INVENTION

The instant invention relates to a process for the preparation of a compound of formula 5:

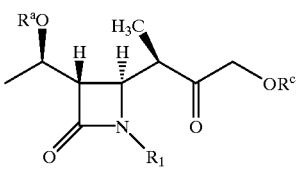

wherein:

$R^a$ is:
(1) hydrogen,
(2) $C_{1-4}$ alkyl or
(3) a hydroxy protecting group; and $R^b$ and $R^c$ are independently:
tri-organo-silyl, including tri-$C_{1-6}$ alkyl silyl, phenyl di-$C_{1-6}$ alkyl silyl, and diphenyl mono $C_{1-6}$ alkyl silyl including tert-butyl-dimethylsilyl, hexyldimethylsilyl and isopropyl dimethylsilyl; straight and branched lower alkyl having from 1 to 10 carbon atoms; alkenyl or alkynyl, having from 2 to 10 carbon atoms; cycloalkyl having from 3 to 6 carbon atoms; cycloalkylalkyl wherein the cycloalkyl moiety comprises 3 to 6 carbon atoms and the alkyl moiety comprises 1 to 10 carbon atoms; alkylcycloalkyl wherein the alkyl moiety comprises 1 to 6 carbon atoms and the cycloalkyl moiety comprises 3 to 6 carbon atoms; aryl, such as phenyl and naphthyl; aralkyl such as benzyl, phenethyl and the like; heterocyclyl (saturated and unsaturated) comprising mono- and bicyclic structures having from 5 to 10 ring atoms, wherein one or more of the heteroatoms is selected from oxygen, nitrogen, or sulfur, such as thiophene, imidazolyl, tetrazolyl,furyl and the like; heterocycloalkyl which comprises the immediately preceding heterocyclyl moieties and the alkyl moiety comprises from 1–10 carbon atoms; substituted species of the above named radicals wherein the substituents are selected from the group consisting of amino, hydroxyl, cyano, carboxyl, nitro, chloro, bromo, or fluoro; lower alkoxy having from 1 to 6 carbon atoms, benzyloxycarbonyl, allyloxycarbonyl and fluorenylmethyloxycarbonyl; mercapto; perhaloloweralkyl such as trifluoromethyl; lower alkylthio; guanidino; amidino; sulfamoyl; N-substituted sulfamoyl, amidino, and guanidino wherein the N-substituent is lower alkyl having from 1 to 6 carbon atoms or aryl having 6–10 carbon atoms; COR or $CO_2R$, wherein R is lower alkyl having from 1 to 6 carbon atoms or aryl having 6–10 carbon atoms; wherein lower alkyl is $C_{1-6}$ alkyl and wherein $R^b$ and $R^c$ may be the same or different, but $R^b$ must be removable in the presence of $R^c$ with the proviso that when $R^a$ is a hydroxy protecting group, $R^b$ and $R^c$ are independently selected from the group consisting of benzyl, ethoxycarbonyl, t-butyloxy, alloxyloxycarbonyl, t-butyldimethylsilyl, and isopropyldimethysilyl; and $R^1$ is an alkylsilyl protecting group corresponding to the silylating agent employed;

comprising: combining the ketoester of formula 4:

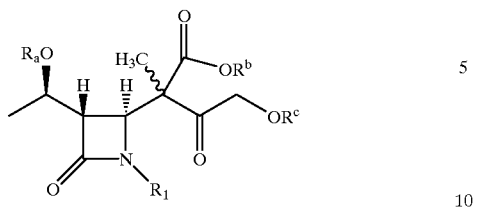

wherein $R^a$, $R^b$, $R^c$ and $R^1$ are described above; with an acid and a first catalyst at a temperature of about 0° C. to about 50° C. with about 0–500 psig $H_2$, to give a compound of formula 5.

This invention also relates to a compound of formula I:

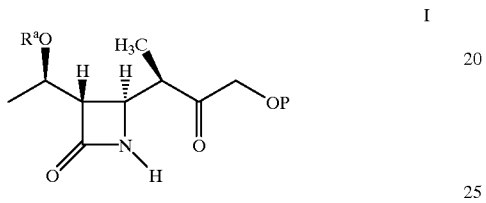

wherein $R_a$ and P are described below and a method of making a compound of formula I.

Other aspects of the invention will be realized upon review of the application as a whole.

DETAILED DESCRIPTION OF THE INVENTION

The instant invention relates to an efficient process for the preparation of beta-methyl intermediates with high stereoselectivity from readily available starting materials. These intermediates can be used to make carbapenem antibiotics as illustrated in Imuta, et al., Chem. Pharm. Bull., 39(3) 672–678 (1991) and Imuta ; et al., Chem. Pharm. Bull., 39(3) 663–671 (1991).

In one embodiment of this invention, a process for synthesizing a compound of formula 6:

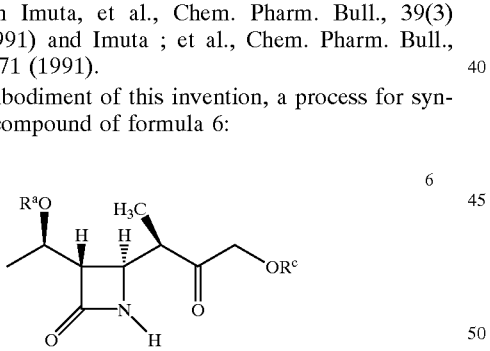

wherein:

$R^a$ is:
(1) hydrogen,
(2) $C_{1-4}$ alkyl or
(3) a hydroxy protecting group; and $R^b$ and $R^c$ are independently:
tri-organo-silyl, including tri-$C_{1-6}$ alkyl silyl, phenyl di-$C_{1-6}$ alkyl silyl, and diphenyl mono $C_{1-6}$ alkyl silyl including tert-butyl-dimethylsilyl, hexyldimethylsilyl and isopropyl dimethylsilyl; straight and branched lower alkyl having from 1 to 10 carbon atoms; alkenyl or alkynyl, having from 2 to 10 carbon atoms; cycloalkyl having from 3 to 6 carbon atoms; cycloalkylalkyl wherein the cycloalkyl moiety comprises 3 to 6 carbon atoms and the alkyl moiety comprises 1 to 10 carbon atoms; alkylcycloalkyl wherein the alkyl moiety comprises 1 to 6 carbon atoms and the cycloalkyl moiety comprises 3 to 6 carbon atoms; aryl, such as phenyl and naphthyl; aralkyl such as benzyl, phenethyl and the like; heterocyclyl (saturated and unsaturated) comprising mono- and bicyclic structures having from 5 to 10 ring atoms, wherein one or more of the heteroatoms is selected from oxygen, nitrogen, or sulfur, such as thiophene, imidazolyl, tetrazolyl, furyl and the like; heterocycloalkyl which comprises the immediately preceding heterocyclyl moieties and the alkyl moiety comprises from 1–10 carbon atoms; substituted species of the above named radicals wherein the substituents are selected from the group consisting of amino, hydroxyl, cyano, carboxyl, nitro, chloro, bromo, or fluoro; lower alkoxy having from 1 to 6 carbon atoms; mercapto; perhaloloweralkyl such as trifluoromethyl; lower alkylthio; guanidino; amidino; sulfamoyl; N-substituted sulfamoyl, amidino, and guanidino wherein the N-substituent is lower alkyl having from 1 to 6 carbon atoms or aryl having 6–10 carbon atoms; COR or $CO_2R$, wherein R is lower alkyl having from 1 to 6 carbon atoms or aryl having 6–10 carbon atoms; wherein lower alkyl is $C_{1-6}$ alkyl and wherein $R^b$ and $R^c$ may be the same or different, but $R^b$ must be removable in the presence of $R^c$ with the proviso that when $R_a$ is a hydroxy protecting group, $R^b$ and $R^c$ are independently selected from the group consisting of benzyl, ethoxycarbonyl, t-butyloxy, benzyloxycarbonyl, allyloxycarbonyl, fluoroenylmethyloxycarbonyl, t-butyldimethylsilyl, and isopropyldimethylsilyl; and comprising: combining the ketoester of formula 4:

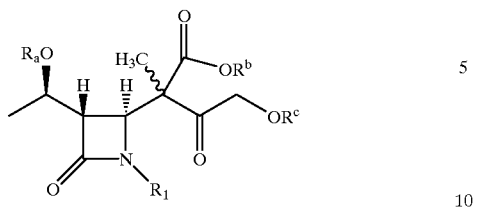

wherein $R^a$, $R^b$, and $R^c$ are defined above and $R^1$ is an alkylsilyl protecting group corresponding to the silylating agent employed;

with an acid and a first catalyst at a temperature of about 0° C. to about 50° C. with about 0–500 psig $H_2$ to give a compound of formula 5:

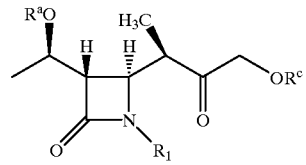

and selectively desilylating with a desilylating agent at a temperature of about −10° C. to about 50° C. to yield the compound of formula 6 is described.

In still another embodiment of the invention, a process for synthesizing a compound of formula I is described:

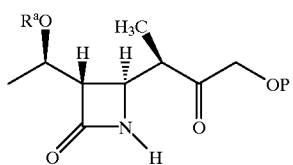

wherein:

R$^a$ and P are independently:
(1) hydrogen,
(2) C$_{1-4}$ alkyl or
(3) a hydroxy protecting group; and comprising:

(a) reacting a ketoester of formula 1:

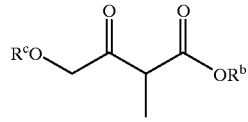

wherein

R$^b$ and R$^c$ are independently:

H, tri-organo-silyl, including tri-C$_{1-6}$ alkyl silyl, phenyl di-C$_{1-6}$ alkyl silyl, and diphenyl mono C$_{1-6}$ alkyl silyl including tert-butyl-dimethylsilyl, hexyldimethylsilyl and isopropyl dimethylsilyl; straight and branched lower alkyl having from 1 to 10 carbon atoms; alkenyl or alkynyl, having from 2 to 10 carbon atoms; cycloalkyl having from 3 to 6 carbon atoms; cycloalkylalkyl wherein the cycloalkyl moiety comprises 3 to 6 carbon atoms and the alkyl moiety comprises 1 to 10 carbon atoms; alkylcycloalkyl wherein the alkyl moiety comprises 1 to 6 carbon atoms and the cycloalkyl moiety comprises 3 to 6 carbon atoms; aryl, such as phenyl and naphthyl; aralkyl such as benzyl, phenethyl and the like; heterocyclyl (saturated and unsaturated) comprising mono- and bicyclic structures having from 5 to 10 ring atoms, wherein one or more of the heteroatoms is selected from oxygen, nitrogen, or sulfur, such as thiophene, imidazolyl, tetrazolyl,furyl and the like; heterocycloalkyl which comprises the immediately preceding heterocyclyl moieties and the alkyl moiety comprises from 1–10 carbon atoms; substituted species of the above named radicals wherein the substituents are selected from the group consisting of amino, hydroxyl, cyano, carboxyl, nitro, chloro, bromo, or fluoro; lower alkoxy having from 1 to 6 carbon atoms; mercapto; perhaloloweralkyl such as trifluoromethyl; lower alkylthio; guanidino; amidino; sulfamoyl; N-substituted sulfamoyl, amidino, and guanidino wherein the N-substituent is lower alkyl having from 1 to 6 carbon atoms or aryl having 6–10 carbon atoms; COR or CO$_2$R, wherein R is lower alkyl having from 1 to 6 carbon atoms or aryl having 6–10 carbon atoms; wherein lower alkyl is C$_{1-6}$ alkyl and wherein R$^b$ and R$^c$ may be the same or different, but R$^b$ must be removable in the presence of R$^c$;

with a compound of formula 2:

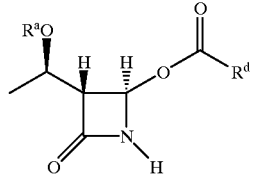

wherein R$^a$ is defined above, and R$^d$ is C$_{1-4}$ alkyl; in the presence of a first base at a temperature of about 25° C. to about 60° C., preferably 35° C. to about 50° C., to produce a ketoester adduct of formula 3:

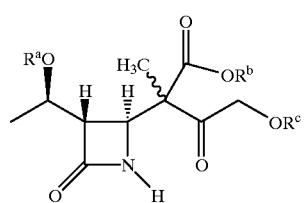

(b) combining the compound of formula 3 with a silylating agent and a second base to produce the ketoester of formula 4:

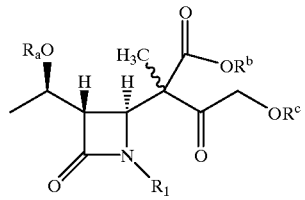

wherein R$^a$, R$^b$, and R$^c$ are defined above and R$^1$ is an alkylsilyl protecting group corresponding to the silylating agent employed;

(c) combining the isolated ketoester of formula 4 with an acid and a first catalyst at a temperature of about 0° C. to about 50° C. with about 0–500 psig H$_2$, to give a compound of formula 5:

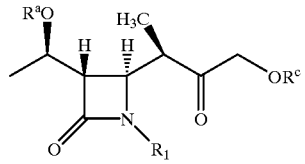

(d) selectively desilylating with a desilylating agent at a temperature of about −10° C. to about 50° C. to yield the compound of formula 6:

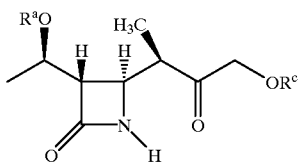

6

(e) dissolving the compound of formula 6 in an alcohol and hydrogenating at about 30 to about 55 psig $H_2$ in the presence of a second catalyst at a temperature of about 0° C. to about 100° C., to yield compound I and (f) purifying and isolating compound I.

A preferred aspect of this embodiment is realized when $R^a$ is a hydroxy protecting group, preferably t-butyldimethylsilyl, and $R^b$ and $R^c$ are independently selected from the group consisting of benzyl, substituted benzyl, ethoxycarbonyl, t-butyloxycarbonyl, benzyloxycarbonyl, allyloxycarbonyl, fluorenylmethyloxycarbonyl, t-butyldimethylsiyl, and isopropyldimethylsilyl, more preferably of benzyl, substituted benzyl, ethoxycarbonyl, or t-butyloxy carbonyl, wherein the benzyl is substituted with 1 to 3 groups of $C_{1-6}$ alkyl, $NO_2$, halogen and the like and all other variables are as described above.

Some of the intermediate compounds synthesized in the present invention occur as diastereomers. The processes of synthesizing all such isomers are included in the present invention.

The desired ketoester of formula 1 can be prepared from corresponding esters, using the standard Claisen condensation technique, as described, for example, in *Organic Chemistry*, L. G. Wade, Jr., Prentice Hall 1991, pp. 1012–1019.

Hydrogenation is carried out with about 0–500 psi $H_2$, preferably 10–100 psi, and more preferably 20–40 psi $H_2$.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, New York (1991). Examples of suitable protecting groups, are: tri-organo-silyl, including tri-$C_{1-6}$ alkyl silyl, phenyl di $C_{1-6}$ alkyl silyl, and diphenyl mono $C_{1-6}$ alkyl silyloxy including tert-butyldimethylsilyl, substituted and unsubstituted benzyl, allyl, triethylsilyl, carbonate esters including t-butyloxycarbonyl, , o-nitrobenzyloxycarbonyl, p-nitrobenzyloxycarbonyl, 2,2,2-trichloroethyloxycarbonyl, benzoylxycarbonyl, allyloxycarbonyl, and fluorenylmethyloxycarbonyl, preferably t-butyldimethyl silyl.

As used herein, "alkyl" is intended to include branched and straight-chain saturated aliphatic hydrocarbon groups having the specified number of carbon atoms. Examples of cycloalkyl groups include cyclopropyl, cyclobutyl, cyclopentyl, cyclohexyl and the like.

As used herein, "heteroaryls" is intended to include both substituted and unsubstituted, carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl or quinolinyl "Aryl" is intended to include aromatic rings e.g., phenyl, substituted phenyl and like groups as well as rings which are fused, e.g., naphthyl and the like. Substitution can be 1 to 3 groups of $C_{1-6}$ alkyl, hydroxy, halogen, carbonyl, $CO_2$, $NO_2$, $OC_{1-6}$ alkyl; $SC_{1-6}$ alkyl , $N(C_{1-6}$ alkyl$)_2$ and the like.

For purposes of this specification, suitable solvents are defined to include a broad spectrum of non-reacting solubilizing agents including: aromatic solvents such as benzene, toluene and xylene; etheral solvents such as diethyl ether, di-n-butyl and diisopentyl ethers, anisole, cyclic ethers such as tetrahydropyran, 4-methyl-1,3-dioxane, dihydropyran, tetrahydrofurfuryl, methyl ether, ethyl ether, furan, 2-ethoxytetrahydrofuran and tetrahydrofuran (THF); ester solvents including ethyl and isopropyl acetate; halo carbon solvents including mono or dihalo $C_{1-4}$ alkyl such as dichloromethane; alcohols, including $C_{1-6}$ alkanol; $C_{6-10}$ linear, branched or cyclic hydrocarbon solvents including hexane; and nitrogen containing solvents including N,N-ethylpyrrolidinone, N,N-dimethylformamide (DMF), N-ethylpyrrolidinone, N-methylpyrrolidinone, and acetonitrile. Preferable solvents are alcohol, EtOAc, isopropyl acetate, hexane, toluene, dichloromethane, THF, DMF, and $CH_3CN$.

Suitable first and second bases are intended to include carbonates, including alkali carbonates such as the potassium and calcium carbonates, diazabicycloundecane (DBU) and tri $C_{1-6}$ alkyl amines, including diisopropylethylamine, triethylamine, dimethylethylamine, dimethylpentylamine and the like. Preferably, the first base is $K_2CO_3$ or DBU. A preferred second base is $Et_3N$ or DBU.

Suitable silylating agents are intended to include trialkylsilylchlorides, triakylsilyliodides, and triflates. In a preferred aspect of this invention, the silylating agent employed is chosen from the group comprising trimethylsilyltriflate (TMSOTf), t-butyl-dimethylsilyltriflate (TBSOTf), triethylsilyltriflate (TESOTf), or t-butyldimethylsilychloride/sodium iodine (TBSCl/NaI). In a more preferred aspect of this invention, the silylating agent is TBSOTf or TBSCl/NaI.

Suitable acids are intended to include mono-, di-, and tri-carboxylic acids, preferably acetic or formic acid.

Suitable desilylating agents are intended to include NaOH, KOH, N-desilylating agents such as tetrabutylammonium fluoride (TBAF), 2-mercaptopyridine N-oxide. Preferably, the desilylation is carried out using an N-desilylating agent such as TBAF in the presence of dichloromethane. Alternatively, N-desilylation is carried out with 2-mercaptopyridine N-oxide as desilylating agent in DMF.

Suitable alcohols are intended to include $C_{1-6}$ alcohols such as methanol, ethanol, 1-propanol, butanol, pentanol, 2-propanol and the like. In a preferred aspect of this invention, the alcohol employed is methanol or ethanol.

Suitable first and second catalysts are intended to include Pd/C, Pd(OH)$_2$/C, or (Ra)Ni (Raney nickel). In a preferred aspect of this invention, Pd/C or Pd(OH)$_2$/C is employed as the first and second catalyst.

In yet another aspect of this invention, a compound of formula I is described:

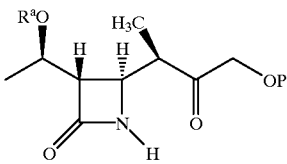

wherein

R<sup>a</sup> and P are:
(1) hydrogen,
(2) C$_{1-4}$ alkyl, or
(3) a hydroxy protecting group.

In a preferred embodiment of this aspect, R<sup>a</sup> is t-butyldimethylsilyl and P is hydrogen, benzyl, ethoxycarbonyl or t-butyloxycarbonyl.

The present invention is illustrated by the following non-limiting reaction scheme and examples:

REACTION SCHEME

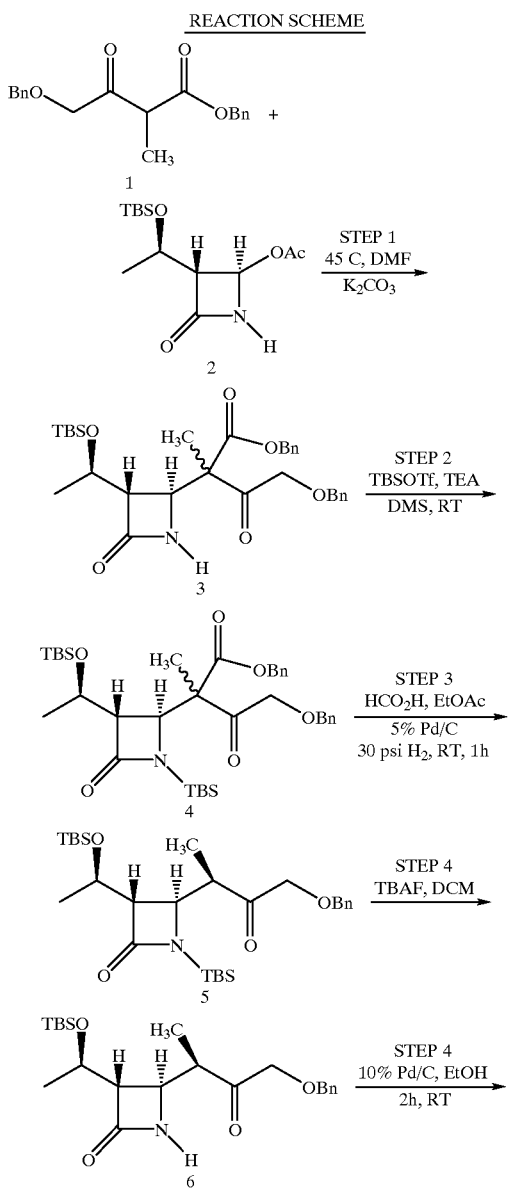

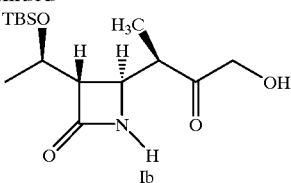

EXAMPLES

Examples provided are intended to assist in a further understanding of the invention. Particular materials employed, species and conditions are intended to be further illustrative of the invention and not limitative of the reasonable scope thereof.

Preparation of the Sidechain KetoEster 1

Benzyl alcohol (54 mL, 500 mmol) was mixed with triethyl amine (86 mL, 600 mmol) in dichloromethane (800 mL). The mixture was cooled to 0° C. and propionyl chloride (46 mL, 500 mmol) was added dropwise. Internal temperature was maintained below 10° C. The mixture was then aged for 1 hr at 0° C. and quenched with water (500 mL). The organic layer was separated, washed with water (300 mL), 2N HCl (300 mL), and concentrated to dryness to give 80 g of a slightly yellow oil. This crude benzyl propionate was used in the upcoming step.

NaH (5.6 g, 60% oil suspension) was washed with hexanes (50 mL) and the wash was decanted. The NaH slurry was then dissolved in a THF/DMF mixture (140 mL/35 mL) and cooled to 0° C. Methyl glycolate (10 mL, 127 mmol) was added dropwise at 0° C. and the mixture was aged for 15 min. Benzyl bromide was then added dropwise at 0° C., and the mixture was allowed to warm up to room temperature ("RT") over 4 hrs. The reaction was quenched with NH$_4$Cl aq. solution and extracted with 9:1 hexane: ethyl acetate mixture (200 mL). The organic layer was washed with water and concentrated to dryness. This crude methyl O-benzyl-glycolate was used in the next step.

Diisopropylamine (14.4 mL, 100 mmol) was dissolved in THF (300 mL) and the mixture was cooled to −40° C. n-BuLi solution (40 mL, 2.5 M in hexane) was added dropwise at −40 to −20° C. The mixture was aged at −70° C. for 1 hour. Benzyl propionate from the previous reaction (16 g, 100 mmol) was added dropwise to the LDA solution at <−70° C. and the mixture was aged at −70° C. for 1 hour. Methyl O-benzyl-glycolate from the previous reaction (8.8 g, 50 mmol) was added to the enolate solution at <−70° C., and the mixture was aged at −70° C. for 1 hour. The reaction was quenched with NH$_4$Cl aq. solution (300 mL) and extracted with ethyl acetate (500 mL). The organic layer was separated, washed with NH$_4$Cl aq. solution (300 mL), water (300 mL), and concentrated to dryness. The resulting oil contained ca. 1:1 mixture of benzyl propionate and the ketoester of formula 1. This crude product was purified by silica gel chromatography eluting with 10:90 ethyl acetate:hexanes, or was used directly in Step 1 and the coupled product later purified by silica gel chromatography using 20:80 ethyl acetate:hexanes mixture. Yield for the Claisen coupling is estimated to be 80% from NMR.

Preparation of Ketoester Adduct 3—Step 1

The crude ketoester (formula 1) from the above reaction (approx. 12 g, 40 mmol) and the acetoxyazetidinone (compound 2) (15 g, 50 mmol) were dissolved in DMF (100 mL). Potassium carbonate (13.9 g, 100 mmol) was added and the mixture aged for 1 hour at 45–50° C. The mixture was then cooled to RT, and quenched with water (300 mL). The mixture was extracted with ethyl acetate (200 mL). The organic layer was separated, washed with 0.2N HCl (200 mL×2) aq. solution and water (100 mL), and concentrated to an oil. Further purification of the oil by silica gel chromatography (20:80 ethyl acetate:hexanes) gave 17.3 g of a 2:1 mixture of diastereomers of the ketoester adduct (formula 3) (32.5 mmol).

Preparation of bis-TBS Ketoester—Step 2

The lactam (formula 3) (8.2 g, 15.4 mmol) was dissolved in dry DMF (30 mL), to which triethylamine (4.5 mL, 30.9 mmol, 2 eq.) and TBSOTf (4.3 mL, 18.5 mmol, 1.2 eq.) were added. The mixture was aged for 1 hour at RT. The reaction mixture was then quenched with water (150 mL) and extracted with ethyl acetate (300 mL). The organic layer was washed with 0.2N HCl aq. solution (100 mL×2) and water (10 mL), and concentrated to dryness to give a colorless oil (10.2 g). In the case where TBSCl is employed, triethylamine (4.5 mL, 1 mmol, 2 eq.), TBSCl (4.52 g, 30 mmol), and NaI (4.50 g, 30 mol) are added to the lactam (8.2 g, 15.4 mol) in dry DMF (30 mL). The mixture is aged at 60 C. for 4 hours and the procedure above is followed.

Preparation of Compound 5 via Decarboxylation—Step 3

The crude ketoester (compound 4)(10.2 g, 15 mmol) was dissolved in ethyl acetate (150 mL). Formic acid (2.1 mL, 45 mmol, 3 eq.) and the catalyst Pd/C (500 mg, 5 w %) were added and the mixture was hydrogenated at 30 psig $H_2$ pressure for 1 hour. The mixture was filtered through a celite pad and the pad was washed with additional ethyl acetate (200 mL) The combined filtrate was washed with saturated sodium bicarbonate solution (50 mL) and water (100 mL) and concentrated to an oil. Further purification of the resulting oil by silica gel chromatography using 10:90 ethyl acetate:hexanes mixture gave 6.2 g of a colorless oil. (12.1 mmol).

N-Desilylation to Compound 6—Step 4

The N-TBS lactam (compound 5)(3.0 g, 5.9 mmol) was dissolved in dichloromethane (50 mL). The solution was cooled to −5° C. and TBAF solution (TBAF in THF IM, 6 mL, 6 mmol) was added dropwise. The mixture was aged for 1 h at −5° C. to 0° C. The reaction was quenched with saturated sodium bicarbonate solution. The organic layer was separated, washed wi aater (3 mL×2), and concentrated to dryness. The resulting oil was purified by silica gel chromatography with a 30:70 ethyl acetate:hexanes mixture to give 1.6 g of an oil.

O-debenzylation of Compound 6—Step 5

The benzyl ether (formula 6)(0.4 g, 1 mmol) was dissolved in ethanol and hydrogenolysed using Pd—C catalyst (40 mg, 10 w %) at 45 psi hydrogen pressure at RT for 2 h. The mixture was then filtered through a pad of Celite and washed with ethyl acetate (30 mL). Combined filtrates were concentrated to dryness. The resulting solid was triturated in hexanes (20 mL) and filtered to give a white solid of compound Ib (230 mg).

What is claimed:

1. A process for synthesizing a compnud of formula 5:

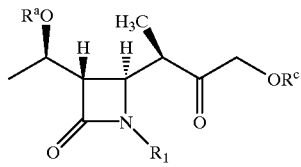

wherein:
$R^a$ is:

(1) hydrogen,
(2) $C_{1-4}$ alkyl or
(3) a hydroxy protecting group; and $R^b$ and $R^c$ are independently:
tri-$C_{1-6}$ alkyl silyl, phenyl di-$C_{1-6}$ alkyl silyl, and diphenyl mono $C_{1-6}$ alkyl silyl selected from tert-butyl-dimethylsilyl, hexyldimethylsilyl and isopropyl dimethylsilyl; straight and branched lower alkyl having from 1 to 10 carbon atoms; alkenyl or alkynyl, having from 2 to 10 carbon atoms; cycloalkyl having from 3 to 6 carbon atoms; cycloalkylalkyl wherein the cycloalkyl moiety comprises 3 to 6 carbon atoms and the alkyl moiety comprises 1 to 10 carbon atoms; alkylcycloalkyl wherein the alkyl moiety comprises 1 to 6 carbon atoms and the cycloalkyl moiety comprises 3 to 6 carbon atoms; aryl, selected from phenyl and naphthyl; aralkyl selected from benzyl and phenethyl; heterocyclyl (saturated and unsaturated) comprising structures having from 5 to 10 ring atoms, wherein one or more of the heteroatoms is oxygen, nitrogen, or sulfur, selected from thiophene, imidazolyl, tetrazolyl, and furyl; heterocycloalkyl which comprises the immediately preceding heterocyclyl moieties and the alkyl moiety comprises from 1–10 carbon atoms; substituted species of the above named radicals wherein the substituents are selected from the group consisting of amino, hydroxyl, cyano, carboxyl, nitro, chloro, bromo, or fluoro; perhaloloweralkyl selected from trifluoromethyl; guanidino; amidino; sulfamoyl; N-substituted sulfamoyl, amidino, and guanidino wherein the N-substituent is lower alkyl having from 1 to 6 carbon atoms or aryl having 6–10 carbon atoms; COR or $CO_2R$, wherein R is lower alkyl having from 1 to 6 carbon atoms or aryl having 6–10 carbon atoms; wherein lower alkyl is $C_{1-6}$ alkyl and wherein $R^b$ and $R^c$ may be the same or different, but $R^b$ must be removable in the presence of $R^c$; and $R^1$ is an alkylsilyl protecting group;
comprising: reacting the ketoester of formula 4;

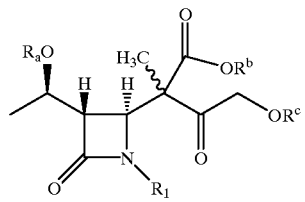

wherein $R^a$, $R^b$, $R^c$ and $R^1$ are described above;
with an acid and a first catalyst selected from Pd/C, Pd(OH)$_2$/C and (Ra)Ni at a temperature of about 0° C. to about 50° C. with about 0–500 psi $H_2$, to give a compound of formula 5.

2. A process according to claim 1 wherein $R_a$ is a hydroxy protecting group and $R^b$ and $R^c$ are independently selected from the group consisting of benzyl, ethoxycarbonyl, t-butyloxy, t-butyloxycarbonyl, t-butyldimethylsilyl, and isoproplydimethylsilyl.

3. A process according to claim 2 wherein $R_a$ is selected from the group consisting of tri-$C_{1-6}$ alkyl silyl, phenyl di $C_{1-6}$ alkyl silyl, diphenyl mono $C_{1-6}$ alkyl silyloxy, tert-butyldimethylsilyl, substituted and unsubstituted benzyl, allyl, triethylsilyl, t-butyloxycarbonyl, o-nitrobenzyloxycarbonyl, p-nitrobenzyloxycarbonyl, 2,2, 2-trichloroethyloxycarbonyl, and $R^b$ and $R^c$ are independently benzyl, substituted benzyl, ethoxycarbonyl, or t-butyloxy carbonyl.

4. A process according to claim 1 wherein $R_a$ is tert-butyldimethylsilyl.

5. A process according to claim 1 wherein the acid is mono-, di-, or tri-carboxylic acid and the first catalyst is Pd/C, Pd(OH)$_2$/C or (Ra)Ni.

6. A process according to claim 5 wherein the acid is acetic acid or formic acid and the first catalyst is Pd/C or Pd(OH)$_2$/C.

7. A process according to claim 1 wherein the reaction is carried out at 10–100 psig H$_2$.

8. A process according to claim 7 wherein the reaction is carried out at 20–40 psig H$_2$.

9. A process for synthesizing a compound of formula 6:

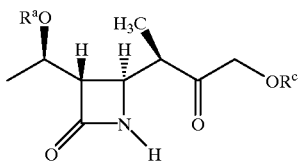

6 wherein:

$R^a$ is:
(1) hydrogen,
(2) $C_{1-4}$ alkyl or
(3) a hydroxy protecting group; and $R^b$ and $R^c$ are independently:
tri-$C_{1-6}$ alkyl silyl, phenyl di-$C_{1-6}$ alkyl silyl, and diphenyl mono $C_{1-6}$ alkyl silyl including tert-butyldimethylsilyl, hexyldimethylsilyl and isopropyl dimethylsilyl; straight and branched lower alkyl having from 1 to 10 carbon atoms; alkenyl or alkynyl, having from 2 to 10 carbon atoms; cycloalkyl having from 3 to 6 carbon atoms; cycloalkylalkyl wherein the cycloalkyl moiety comprises 3 to 6 carbon atoms and the alkyl moiety comprises 1 to 10 carbon atoms; alkylcycloalkyl wherein the alkyl moiety comprises 1 to 6 carbon atoms and the cycloalkyl moiety comprises 3 to 6 carbon atoms; aryl, selected from phenyl and naphthyl; aralkyl selected from benzyl and phenethyl; heterocyclyl (saturated and unsaturated) comprising structures having from 5 to 10 ring atoms, wherein one or more of the heteroatoms is selected from oxygen, nitrogen, or sulfur, wherein the structure is selected from thiophene, imidazolyl, tetrazolyl and furyl; heterocycloalkyl which comprises the immediately preceding heterocyclyl moieties and the alkyl moiety comprises from 1–10 carbon atoms; substituted species of the above named radicals wherein the substituents are selected from the group consisting of amino, hydroxyl, cyano, carboxyl, nitro, chloro, bromo, or fluoro; perhaloloweralkyl selected from trifluoromethyl; guanidino; amidino; sulfamoyl; N-substituted sulfamoyl, amidino, and guanidino wherein the N-substituent is lower alkyl having from 1 to 6 carbon atoms or aryl having 6–10 carbon atoms; COR or CO$_2$R, wherein R is lower alkyl having from 1 to 6 carbon atoms or aryl having 6–10 carbon atoms; wherein lower alkyl is $C_{1-6}$ alkyl and wherein $R^b$ and $R^c$ may be the same or different, but $R^b$ must be removable in the presence of $R^c$;

comprising: reacting the ketoester of formula 4:

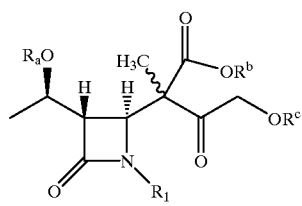

wherein $R^a$, $R^b$, and $R^c$ are defined above and $R^1$ is an alkylsilyl protecting group; with an acid and a first catalyst selected from Pd/C, Pd(OH)$_2$/C and (Ra)Ni at a temperature of about 0° C. to about 50° C. with about 0–500 psi H$_2$ to give a compound of formula 5:

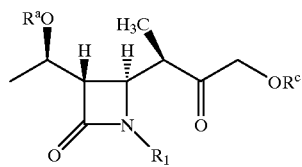

and selectively desilylating with a desilylating agent selected from NaOH, KOH, tetrabutylammonium fluoride and 2-mercaptopyridine N-oxide at a temperature of about —10° C. to about 50° C. to yield the compound of formula 6.

10. A process according to claim 9 wherein $R_a$ is a hydroxy protecting group and $R^b$ and $R^c$ are independently selected from the group consisting of benzyl, substituted benzyl, ethoxycarbonyl, t-butyloxy, t-butyldimethylsilyl, and isopropyldimethylsilyl.

11. A process according to claim 10 wherein $R_a$ is selected from the group consisting of tri-$C_{1-6}$ alkyl silyl, phenyl di $C_{1-6}$ alkyl silyl, diphenyl mono $C_{1-6}$ alkyl silyloxy, tert-butyldimethylsilyl, substituted and unsubstituted benzyl, allyl, triethylsilyl, t-butyloxycarbonyl, o-nitrobenzyloxycarbonyl, p-nitrobenzyloxycarbonyl, 2,2,2-trichloroethyloxycarbonyl, and $R^b$ and $R^c$ are independently benzyl, substituted benzyl, ethoxycarbonyl, or t-butyloxy carbonyl.

12. A process according to claim 10 wherein $R_a$ is tert-butyldimethylsilyl.

13. A process according to claim 10 wherein the desilylating agent is selected from the group consisting of NaOH, KOH, the acid is mono-, di-, or tri-carboxylic acid and N-desilylating agent and the first catalyst is Pd/C, Pd(OH)$_2$/C or (Ra)Ni.

14. A process according to claim 13 wherein the desilylating agent is an N-desilylating selected from the group consisting of TBAF or 2-mercaptopyridine N-oxide, the acid is acetic acid or formic acid and the first catalyst is Pd/C or Pd(OH)$_2$/C.

15. A process according to claim 10 wherein the reaction is carried out at 10–100 psig H$_2$.

16. A process according to claim 15 wherein the reaction is carried out at 20–40 psig H$_2$.

17. A process for synthesizing a compound of formula I:

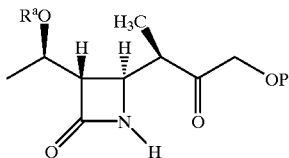

I wherein:
$R^a$ is:
(1) hydrogen,
(2) $C_{1-4}$ alkyl or
(3) a hydroxy protecting group;
and P is hydrogen, comprising:
(a) reacting a ketoester of formula 1:

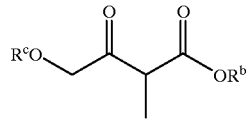

1 wherein $R^b$ is selected from H, tri-$C_{1-6}$ alkyl silyl, phenyl di-$C_{1-6}$ alkyl silyl, and diphenyl mono $C_{1-6}$ alkyl silyl including tert-butyl-dimethylsilyl, hexyldimethylsilyl and isopropyl dimethylsilyl; straight and branched lower alkyl having from 1 to 10 carbon atoms; alkenyl or alkynyl, having from 2 to 10 carbon atoms; cycloalkyl having from 3 to 6 carbon atoms; cycloalkylalkyl wherein the cycloalkyl moiety comprises 3 to 6 carbon atoms and the alkyl moiety comprises 1 to 10 carbon atoms; alkylcycloalkyl wherein the alkyl moiety comprises 1 to 6 carbon atoms and the cycloalkyl moiety comprises 3 to 6 carbon atoms; aryl selected from phenyl and naphthyl; aralkyl selected from benzyl and phenethyl; heterocyclyl (saturated and unsaturated) comprising structures having from 5 to 10 ring atoms, wherein one or more of the heteroatoms is selected from oxygen, nitrogen, and sulfur, wherein the structure is selected from thiophene, imidazolyl, tetrazolyl and furyl; heterocycloalkyl which comprises the immediately preceding heterocyclyl moieties and the alkyl moiety comprises from 1–10 carbon atoms; substituted species of the above named radicals wherein the substituents are selected from the group consisting of amino, hydroxyl, cyano, carboxyl, nitro, chloro, bromo, or fluoro; perhaloloweralkyl selected from trifluoromethyl; guanidino; amidino; sulfamoyl; N-substituted sulfamoyl, amidino, and guanidino wherein the N-substituent is lower alkyl having from 1 to 6 carbon atoms or aryl having 6–10 carbon atoms; COR or $CO_2R$, wherein R is lower alkyl having from 1 to 6 carbon atoms or aryl having 6–10 carbon atoms; and $R^c$ is selected from the group consisting of tri-$C_{1-6}$ alkyl silyl, phenyl di-$C_{1-6}$ alkyl silyl, and diphenyl mono $C_{1-6}$ alkyl silyl including tert-butyl-dimethylsilyl, hexyldimethylsilyl and isopropyl dimethylsilyl; straight and branched lower alkyl having from 1 to 10 carbon atoms; alkenyl or alkynyl, having from 2 to 10 carbon atoms; cycloalkyl having from 3 to 6 carbon atoms; cycloalkylalkyl wherein the cycloalkyl moiety comprises 3 to 6 carbon atoms and the alkyl moiety comprises 1 to 10 carbon atoms; alkylcycloalkyl wherein the alkyl moiety comprises 1 to 6 carbon atoms and the cycloalkyl moiety comprises 3 to 6 carbon atoms; aryl selected from phenyl and naphthyl; aralkyl selected from benzyl and phenethyl; heterocyclyl (saturated and unsaturated) comprising structures having from 5 to 10 ring atoms, wherein one or more of the heteroatoms is selected from oxygen, nitrogen, and sulfur, wherein the structure is selected from thiophene, imidazolyl, tetrazolyl and furyl; heterocycloalkyl which comprises the immediately preceding heterocyclyl moieties and the alkyl moiety comprises from 1–10 carbon atoms; substituted species of the above named radicals wherein the substituents are selected from the group consisting of amino, hydroxyl, cyano, carboxyl, nitro, chloro, bromo, or fluoro; perhaloloweralkyl selected from trifluoromethyl; guanidino; amidino; sulfamoyl; N-substituted sulfamoyl, amidino, and guanidino wherein the N-substituent is lower alkyl having from 1 to 6 carbon atoms or aryl having 6–10 carbon atoms; COR or $CO_2R$, wherein R is lower alkyl having from 1 to 6 carbon atoms or aryl having 6–10 carbon atoms; wherein R is lower alkyl having from 1 to 6 carbon atoms or aryl having 6–10 carbon atoms; wherein lower alkyl is $C_{1-6}$ alkyl and wherein $R^b$ and $R^c$ may be the same or different, but $R^b$ must be removable in the presence of $R^c$;

with a compound of formula 2:

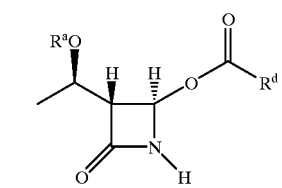

2 wherein $R_a$ is defined above, and $R^d$ is $C_{1-4}$ alkyl;
in the presence of a first base selected from potassium and calcium carbonates, diazabicycloundecane, diisopropylethylamine, triethylamine, dimethylethylamine and dimethylpentylamine at a temperature of about 25° C. to about 60° C. to produce a ketoester adduct of formula 3:

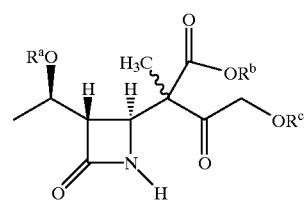

3

(b) reacting the compound of formula 3 with a silylating agent and a second base to produce the ketoester of formula 4:

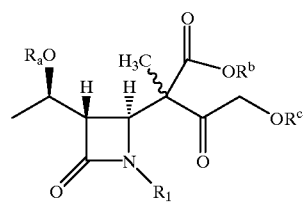

4 wherein $R^a$, $R^b$, and $R^c$ are defined above and $R^1$ is an alkylsilyl protecting group;

(c) reacting the isolated ketoester of formula 4 with an acid and a first catalyst at a temperature of about 0° C. to about 50° C. with about 0–500 psi H$_2$, to give a compound of formula 5:

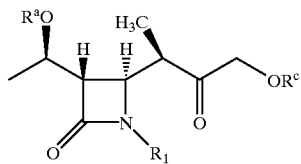

(d) selectively desilylating with a desilylating agent at a temperature of about −10° C. to about 50° C. to yield the compound of formula 6:

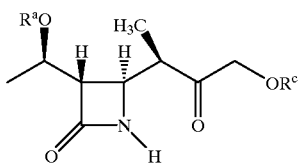

(e) dissolving the compound of formula 6 in an alcohol and hydrogenating at about 30 to about 55 psi with H$_2$ in the presence of a second catalyst selected from Pd/C, Pd(OH)$_2$/C and (Ra)Ni at a temperature of about 0° C. to about 100° C., to yield the compound of formula 1; and (f) purifying and isolating the compound of formula.

18. A process according to claim 17 wherein R$_a$ is a hydroxy protecting group and R$^b$ and R$^c$ are independently selected from the group consisting of benzyl, substituted benzyl, ethoxycarbonyl, t-butyloxycarbonyl, t-butyldimethylsilyl, and isopropyldimethylsilyl.

19. A process according to claim 18 wherein R$_a$ is selected from the group consisting of tri-C$_{1-6}$ alkyl silyl, phenyl di C$_{1-6}$ alkyl silyl, diphenyl mono C$_{1-6}$ alkyl silyloxy, tert-butyldimethylsilyl, substituted and unsubstituted benzyl, allyl, triethylsilyl, t-butyloxycarbonyl, o-nitrobenzyloxycarbonyl, p-nitrobenzyloxycarbonyl, 2,2, 2-trichloroethyloxycarbonyl, and R$^b$ and R$^c$ are independently H, benzyl, substituted benzyl, ethoxycarbonyl, or t-butyloxy carbonyl.

20. A process according to claim 17 wherein R$^a$ is tert-butyldimethylsilyl.

21. A process according to claim 17 wherein the reaction at step (c) is carried out at 10–100 psig H$_2$.

22. A process according to claim 21 wherein the reaction is carried out at 20–40 psig H$_2$.

23. A process according to claim 17 wherein the first and second bases are selected from the group consisting of potassium carbonate, calcium carbonate, diisopropylethylamine, triethylamine, dimethylethylamine, dimethylpentylamine and diazabicycloundecane; the silylating agent is selected from the group consisting of trialkylsilylchlorides, trialkylsilyliodides and trimethylsilyltriflate, t-butyldimethylsilyltriflate, triethylsilyltriflate and t-butyldimethylsilylchloride/sodium iodide and the desilylating agent is selected from the group consisting of NaOH, KOH, and tetrabutylammonium floride, and 2-mercaptopyridine N-oxide; and 24. A process according to claim 3 wherein the first base is potassium carbonate or diazabicycloundecane, the second base is triethylamine or diazabicycloundecane; the silyating agent is trimethylsilyltriflate, t-butyldimethylsilytriflate, triethylsilytriflate and t-butyldimethylsilychloride/sodium iodide; and the desilylating agent is an selected from the group consisting of tetrabutylammonium fluoride or 2-mercaptopyridine N-oxide.

25. A process according to claim 17 wherein the acid is mono-, di-, or tri-carboxylic acid; the alcohol is methanol, ethanol, butanol, pentanol, 1-propanol or 2-propanol and the first and second catalyst are Pd/C, Pd(OH)$_2$/C or (Ra)Ni.

26. A process according to claim 25 wherein the acid is acetic acid or formic acid; the alcohol is methanol or ethanol and the first and second catalyst are Pd/C or Pd(OH)$_2$/C.

* * * * *

UNITED STATES PATENT AND TRADEMARK OFFICE
CERTIFICATE OF CORRECTION

PATENT NO. : 6,143,885
DATED : November 7, 2000
INVENTOR(S) : Woo-Baeg Choi, Joemoon Lee, Joseph E. Lynch, Paul J. Reider, Ralph P. Volante It is certified that error appears in the above-identified patent and that said Letters Patent is hereby corrected as shown below:

(1) In claim 2, column 12, line 57;
claim 3, column 12, line 62;
claim 4, column 13, line 4;
claim 11, column 14, line 50, and
claim 19, column 17, line 39,
after the word "wherein", the word should read as follows:

-- $R^a$ -- .

(2) In claim 24, column 18, line 33 should read as follows:

-- 24. A process according to claim 23 wherein the first base -- .

(3) In claim 24, column 18, line 29, after the word "and", should read:

Signed and Sealed this

Twenty-ninth Day of May, 2001

Attest:

NICHOLAS P. GODICI

*Attesting Officer*     *Acting Director of the United States Patent and Trademark Office*

UNITED STATES PATENT AND TRADEMARK OFFICE
CERTIFICATE OF CORRECTION

PATENT NO. : 6,143,885
DATED : November 7, 2000
INVENTOR(S) : Woo-Baeg Choi et al.

It is certified that error appears in the above-identified patent and that said Letters Patent is hereby corrected as shown below:

Column 12,
Lines 57 and 62, after the word "wherein", the word should read as follows: -- $R^a$ --.

Column 13,
Line 4, after the word "wherein", the word should read as follows: -- $R^a$ --.

Column 14,
Line 50, after the word "wherein", the word should read as follows: -- $R^a$ --; and Column 17,
Line 39, after the word "wherein", the word should read as follows: -- $R^a$ --.

Column 18,
Line 33, should read as follows: -- 24. A process according to claim 23 wherein the first base --.
Line 29, after the word "and", should read: -- t-butyldimethylsilylchloride/sodium --.

This certificate supersedes Certificate of Correction issued May 29, 2001.

Signed and Sealed this

Eleventh Day of May, 2004

JON W. DUDAS
*Acting Director of the United States Patent and Trademark Office*